United States Patent [19]

Cross et al.

[11] 3,931,222

[45] Jan. 6, 1976

[54] TETRAHYDRO-CARBAZOLE DERIVATES

[75] Inventors: Peter E. Cross, Canterbury; Roger P. Dickinson, Worth, near Deal; John E. G. Kemp, Canterbury, all of England

[73] Assignee: Pfizer Inc., New York, N.Y.

[22] Filed: May 29, 1974

[21] Appl. No.: 474,151

[30] Foreign Application Priority Data
June 2, 1973 United Kingdom............... 26414/73

[52] U.S. Cl.......... 260/315; 260/243 R; 260/243 B; 260/239 B; 260/247.5 R; 260/247.5 FP; 260/293.61; 260/293.79; 260/326.5 L; 260/326.86; 260/569; 424/246; 424/248; 424/267; 424/274
[51] Int. Cl.²...................................... C07D 209/86
[58] Field of Search...... 260/315, 293.61, 247.5 FP, 260/243 B, 243 R

[56] References Cited
UNITED STATES PATENTS

| | | | |
|---|---|---|---|
| 2,541,211 | 2/1951 | Cusic et al. | 260/247.5 FP |
| 3,663,567 | 5/1972 | Eberle | 260/315 |

OTHER PUBLICATIONS
J. Med. Chem. 13:327–328 (1970), Pecca et al.

*Primary Examiner*—Sherman D. Winters
*Attorney, Agent, or Firm*—Connolly and Hutz

[57] ABSTRACT

Novel 3-alkyl-9-aminoalkyl-1,2,3,4-tetrahydrocarbazoles having gastric anti-secretory activity are prepared. A typical embodiment is 3-tertiary-butyl-9-(2-pyrrolidino-ethyl)-1,2,3,4-tetrahydrocarbazole.

7 Claims, No Drawings

TETRAHYDRO-CARBAZOLE DERIVATES

BACKGROUND OF THE INVENTION

The invention relates to compounds having antisecretory activity, and is particularly concerned with a class of novel 3-alkyl-9-aminoalkyl-1,2,3,4-tetrahydrocarbazoles which are capable of selectively inhibiting gastric acid secretion without causing bronchial constriction or other side effects. These compounds are therefore useful in the treatment of peptic ulcers and other conditions caused or exacerbated by gastric hyperacidity.

SUMMARY OF THE INVENTION

The novel compounds of the invention have the general formula:

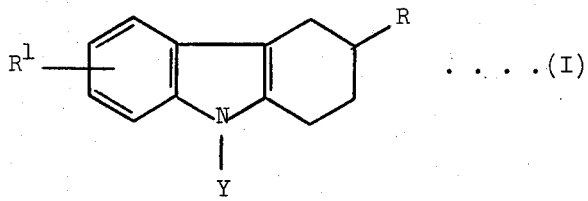

. . . . (I)

the N-oxides and the pharmaceutically-acceptable acid addition salts thereof wherein R is alkyl of from 3 to 5 carbon atoms, $R^1$ is hydrogen, halogen, lower alkyl, lower alkoxy or hydroxy; and Y is aminoalkyl of the formula $-Alk-NR^2R^3$ in which $R^2$ and $R^3$ taken separately are each lower alkyl and $R^2$ and $R^3$ taken together with the nitrogen atom to which they are attached form a pyrrolidino, piperidino, perhydroazepino, morphilino, thiomorpholino or 1,1-dioxoperhydro-1,4-thiazino group and 'Alk' is a divalent alkyl group containing from 2 to 4 carbon atoms; or Y is an amino-cyclic group of the formula $-C_nH_{2n}-CH\angle Z$, in which n is 0 to 3 and Z is a divalent group which completes a pyrrolidine, piperidine or perhydroazepine ring, the nitrogen atom in said ring being separated from the nitrogen atom to which the aminocyclic group is attached by a chain of from 2 to 4 carbon atoms.

In addition, there is disclosed a composition in unit dosage form useful for alleviating excess gastric acid secretion in a host comprising a pharmaceutical carrier containing from about 25 mg to about 500 mg of a compound of formula I.

DETAILED DESCRIPTION OF THE INVENTION

In the general formula, R may be a straight or branched chain alkyl group. For example, it may be a n-propyl, iso-propyl, n-butyl, sec-butyl, or tert-butyl group or any of the pentyl groups. Preferably, it is a branched chain alkyl group containing a quaternary carbon atom, e.g. a tert-butyl, tert-pentyl or neo-pentyl group.

When Y is a $-Alk-NR^2R^3$ group, $R^2$ and $R^3$ may each be, for example, a methyl, ethyl, propyl or butyl group, or together with the nitrogen atom may form, for example, a pyrrolidino, piperidino, perhydroazepino, morpholino, thiomorpholino or 1,1-dioxoperhydro-1,4-thiazino group.

When Y is a $-Alk-NR^2R^3$ group, $-Alk-$ may be, for example, an ethylene, propylene, ethyl-substituted ethylene, dimethyl-substituted ethylene, trimethylene or tetramethylene group.

When Y is a $-C_nH_{2n}-CH\angle Z$ group, $-C_nH_{2n}-$ may be, for example, a direct link or a methylene, ethylidene, ethylene, propylene or trimethylene group, and the heterocyclic ring completed by Z may be, for example, a pyrrolidine, piperidine or perhydroazepine ring, provided that the nitrogen atom in the ring is separated by at least 2 carbon atoms from the nitrogen atom to which the group Y is attached.

Thus, $-C_nH_{2n}-CH\angle Z$ may be, for example, a 3-pyrrolindinyl or 3- or 4-piperidyl group, a 2- or 3-pyrrolidinylmethyl or 2-, 3- or 4-piperidylmethyl group, a 2-(2- or 3-pyrrolidinyl) ethyl or 2-(2- or 3-piperidyl) ethyl group, or a 3-(2-pyrrolidinyl) propyl or 3-(2-piperidyl)- propyl group, or any corresponding group in which piperidinyl is replaced by perhydroazepinyl. Any nitrogen atom in Z is preferably substituted with a lower alkyl or a benzyl group, while any carbon atom in $-CH\angle Z$ may be substituted with a lower alkyl group.

Throughout this specification, the term 'lower alkyl group' means one which contains from 1 to 4 carbon atoms, and 'halogen' means fluorine, chlorine, bromine or iodine.

Pharmaceutically-acceptable acid addition salts of the compounds of the invention can be prepared from acids which form non-toxic addition salts containing pharmaceutically-acceptable anions, such as the hydrochloride, hydrobromide, hydriodide, sulfate or bisulfate, phosphate or acid phosphate, acetate, maleate, fumarate, oxalate, lactate, tartrate, citrate, gluconate, saccharate, and p-toluene sulfonate salts.

The compounds of the invention may be prepared in a number of ways, including the following:

1. An appropriate 3-alkyl-1,2,3,4-tetrahydrocarbazole is reacted first with an alkali metal compound in an inert solvent to form the alkali metal derivative of the carbazole, and then with
   a. the appropriate halide, of the formula : hal—Alk—$NR^2R^3$ or hal—$C_nH_{2n}$—$CH\angle Z$, where 'hal' represents a halogen atom, to yield the required product directly; or
   b. a compound of the formula : hal—Alk—Q, where Q represents a halogen atom or a 'leaving' group, e.g. an aryl sulfonyloxy group such as benzene sulfonyloxy or p-toluene sulfonyloxy, to form a compound of the formula:

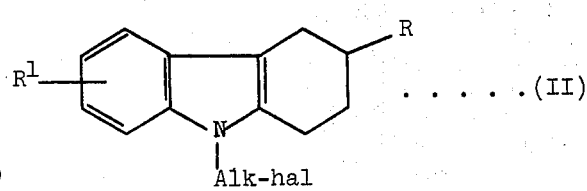

. . . . . (II)

which is then reacted with the appropriate secondary amine $HNR^1R^2$, thus affording a compound of the formula (I) in which Y represents an aminoalkyl group of the formula —Alk—NR²R³; or c. a halo-alkanol or the formula : hal—Alk—OH, to form a compound of the formula:

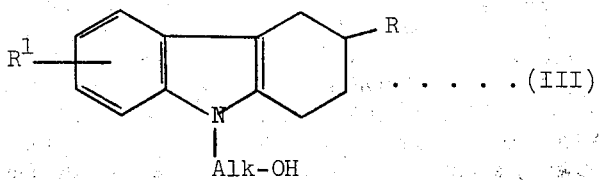

(III)

which is then converted to the halide, e.g. by reaction with thionyl chloride, the product then being reacted with the appropriate secondary amine as in (b).

The formation of the alkali metal derivative of the carbazole may be carried out by adding sodium hydride or sodamide portionwise to a solution of the carbazole in an inert solvent, e.g. toluene or dimethylformamide, and then heating. Reaction with one of the halides denoted in methods (a), (b) and (c) may then be carried out by heating e.g. at reflux temperature. Subsequent reaction in methods (b) and (c) with the secondary amine may be carried out in any suitable inert solvent, e.g. benzene, under reflux conditions.

In each method the final product, as the free base, may be isolated by collection of a precipitate (if necessary, formed by addition of water) by filtration, or by removal of solvent under reduced pressure, addition of water, extraction into a suitable solvent, e.g. diethyl ether, drying and evaporation under reduced pressure, or by addition of water to the cooled reaction mixture, extraction into a suitable solvent, e.g. diethyl ether, drying and evaporation under reduced pressure. A solid product may be purified by recrystallization from a suitable solvent, and a liquid product by distillation, preferably under reduced pressure. In both cases an acid addition salt may be obtained in the usual manner by addition of the appropriate acid in a suitable solvent to a solution of the product in the same solvent, or to the neat product if a liquid, and collection of the precipitate. The salt may then be purified further if necessary by recrystallization from a suitable solvent.

In each of the above methods, the starting 3-alkyl-1,2,3,4,-tetrahydrocarbazoles are known compounds or are readily preparable from phenyl hydrazine and the appropriate 4-alkylcyclohexanone by analogous procedures to those reported in the literature, for example, in J. Am. Chem. Soc., 69,2910 (1947) and Proc. Okla. Acad. Sci., 47, 215 (1968).

2. A phenylhydrazine derivative of the formula:

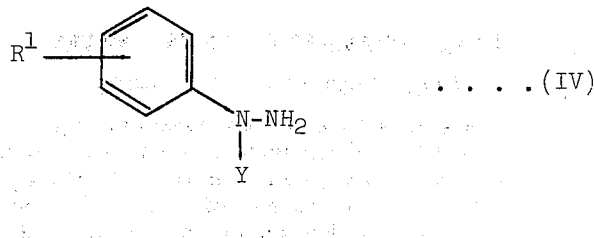

(IV)

is reacted with a 4-alkylcyclohexanone in the presence of an acid, e.g. sulfuric or acetic acid, suitably by heating under reflux, to afford the required product of the formula (I) directly. The detailed procedure for performing the reaction and isolating the product is analogous to procedures described in the literature, for example, in German Pat. No. 530,496.

3. The N-oxides of the compounds of the formula (I) may be prepared from the corresponding compounds of the formula (I) by reaction with an oxidizing agent such as hydrogen peroxide.

In a typical procedure, a mixture of the starting 3-alkyl-9-aminoalkyl-1,2,3,4-tetrahydrocarbazole and 30% aqueous hydrogen peroxide solution, containing theoretical quantity of $H_2O_2$, in glacial acetic acid is maintained at room temperature for several days, and the solution is then evaporated to dryness. The residue is distributed between organic and aqueous phases, the latter being basic to remove excess acid, and the organic phase is separated and evaporated to dryness, to isolate the crude product. Purification and/or conversion of the latter into an acid addition salt may be effected using standard procedures.

In another typical procedure, the starting carbazole and an excess quantity of 30% aqueous hydrogen peroxide solution in methanol are stirred at room temperature for several days, after which the excess hydrogen peroxide is decomposed by addition of a small quantity of platinum on charcoal or potassium permangate. The sediment is removed by filtration, and the filtrate is evaporated to dryness to afford the crude product, which may be purified and/or converted to an acid addition salt as desired.

All the compounds of the invention contain an asymmetric center at the carbon atom bearing the alkyl group, R, and the latter and groups represented by Y in particular cases also contain asymmetric centers. Thus the compounds containing one or more asymmetric centers will exist as one or more pairs of enantiomers. Such pairs or individual isomers may be separable by physical methods, e.g. by fractional crystallization or chromatography of the free base or suitable salts, e.g. salts formed with optically-active acids. The invention includes the separated pairs as well as mixtures thereof, as racemic mixtures or As separated D- and L- optically-active forms.

The compounds of formula (I) have been found to be potent inhibitors of gastric acid secretion induced by histamine. This has been shown in tests in which their inhibiting effect on histamine-induced gastric acid secretion has been measured in experimental animals. In such tests, anaesthetized rats are sensitized by intravenous injection of carbachol (carbamoyl choline chloride) and are then injected intravenously with a standard dose of histamine and the pH of the gastric contents is measured over a short period, until it stabilizes.

The test compound is then administered, also intravenously, and the pH of the gastric contents is measured over a further period, until the inhibiting effect of the compound is no longer apparent. In similar tests with anaesthetized cats, histamine is continuously infused before and during administration of the test compound.

By virtue of their inhibiting activity, the compounds of formula (I) are useful for reducing gastric hyper-acidity and therefore in the treatment of peptic ulcers and other conditions caused or exacerbated by gastric hyper-acidity.

The compounds of the invention can be administered alone, but will generally be administered in admixture with a pharmaceutical carrier or diluent selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally, for example, intramuscularly or subcutaneously. For parenteral administration, they are best used in the form of a sterile aqueous which may contain other solutes, for example, enough salts or glucose to make the solution isotonic.

As a result of testing in animals, the more effective compounds of the invention have been found to be those in which R is a tert-butyl group, $R^1$ is hydrogen or halogen atom and Y is an amino-alkyl group —Alk-—$NR^2R^3$ in which 'Alk' is ethylene or trimethylene, particularly those in which —$NR^2R^3$ is a dimethylamino, diethylamino, pyrrolidino, piperidino, perhydroazepino or morpholino group. Such compounds have been found to give at least 75% inhibition of the effect of histamine on gastric acid secretion in rats when administered intravenously at doses of 5mg/kg, the most active being 3-tert-butyl-9-(2-pyrrolidinoethyl)-1,2,3,4-tetrahydrocarbazole, which has been found to give 100% inhibition at 5mg/kg over a period of 3 hours or more after injection.

With respect to dosage levels for human administration, it is expected that a broad dosage range of from 25 to 500 mg for adults will be appropriate, with a preferred range of from 100 to 250 mg, such dosage being administrable up to four times a day. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

The invention is illustrated by the following Examples.

EXAMPLE 1

Sodium hydride (1.20g; 50% dispersion in oil) was added to a solution of 3-tert-butyl-1,2,3,4-tetrahydrocarbazole (5.68g) in dry dimethylformamide (25ml) and the mixture was heated over a steam bath for one-half hour. 2-Pyrrolidinoethyl chloride (3.34g) was then added, and the mixture was heated over the steam bath for a further 4 hours. Thereafter the mixture was cooled at room temperature, allowed to stand for about 16 hours, and poured into water. The aqueous mixture was extracted with diethyl ether, and the ethereal solution was evaporated in vacuo to afford 3-tert-butyl-9-(2-pyrrolidinoethyl)-1,2,3,4-tetrahydrocarbazole as an oil. The latter was distilled under reduced pressure, the principal fraction collected having a b.p. of 185°–195°C/0.05mm. mercury pressure.

Conversion of the oil product into the hydrochloride salt by conventional means was followed by recrystallization from a mixture ethanol and diethyl ether, to afford 3.85 g of the corresponding hydrochloride m.p. 255°–8°C.

Analysis: Found: C, 73.01; H, 9.30; N, 8.08%. Calc'd. for $C_{22}H_{32}N_2.HCl$: C, 73.18; H, 9.21; N, 7.76%.

EXAMPLES 2 TO 6

By methods similar to that of Example 1 the compounds shown in the following examples were prepared from 3-tert-butyl-1,2,3,4-tetrahydrocarbazole and the appropriate chloride Y—Cl, and characterized as the salt indicated.

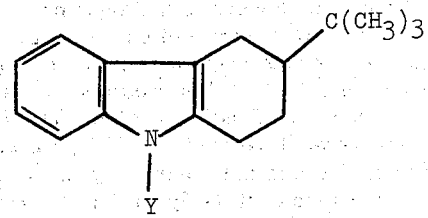

| Example | Y | Isolated as | M.P. °C | Analysis % (Theoretical in brackets) | | |
|---|---|---|---|---|---|---|
| | | | | C | H | N |
| 2 | —(CH₂)₃N(CH₃)₂ | Hydrochloride | 222–5 | 72.54 (72.49 | 9.45 9.27 | 8.22 8.05) |
| 3 | —(CH₂)₂N(C₂H₅)₂ | oxalate | 183–5 | 69.00 (69.21 | 8.80 8.71 | 6.59 6.72) |
| 4 | —(CH₂)₂N⌬O | oxalate | 240–2 | 66.92 (66.91 | 7.98 7.96 | 6.67 6.51) |
| 5 | —(CH₂)₂N⌬ | Hydrochloride | 249–252 | 74.11 (74.09) | 9.75 (9.59) | 7.46 (7.2) |
| 6 | —(CH₂)₂N⌬SO₂ | free base | 183–6 | 67.87 (67.98) | 8.56 (8.30) | 7.10 (7.21) |

EXAMPLES 7 to 22

The compounds indicated in the following examples are prepared by methods similar to that of Example 1 from the appropriate tetrahydrocarbazole and chloride Y—Cl.

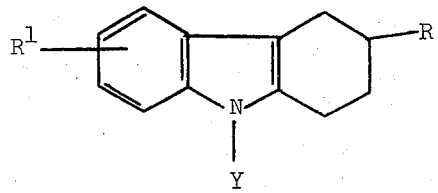

| Example | R | R¹ | Y |
|---|---|---|---|
| 7 | tert-pentyl | H | 2-pyrrolidino-ethyl |
| 8 | neo-pentyl | H | '' |
| 9 | tert-butyl | 6—Cl | '' |
| 10 | '' | 7—Cl | '' |
| 11 | '' | 8—Cl | '' |
| 12 | '' | 6—F | 2-piperidino-ethyl |
| 13 | '' | 6—CH₃ | '' |
| 14 | '' | 6—CH₃O | 2-perhydroazepino-ethyl |
| 15 | '' | 8—CH₃O | '' |
| 16 | '' | 6—HO | '' |
| 17 | '' | 8—HO | '' |
| 18 | '' | H | 2-thiomorpholino-ethyl |
| 19 | '' | H | 1-ethyl-2-pyrrolidinyl-methyl |
| 20 | '' | H | 1-methyl-2-(2-pyrrolidinyl)-ethyl |
| 21 | '' | H | 1-methyl-2-piperidinyl-methyl |
| 22 | '' | H | 1-methyl-2-perhydroazepinyl-methyl |

EXAMPLE 23

The product of Example 1 as free base (22.25g) in methanol (300 ml) was cooled to 0° (ice/water bath). Aqueous 30% w/v hydrogen peroxide (31.4g) was added dropwise over about 15 minutes, with cooling and stirring. The mixture was kept at ambient temperature for 3 days, and the excess hydrogen peroxide was then decomposed with a trace of potassium permanganate. The mixture was evaporated to dryness and the residue was dissolved in hot isopropanol (40 ml). Water (500 ml) was added with stirring and the mixture was refrigerated overnight, yielding a precipitate which was dissolved in hot water, filtered, and cooled, yielding a precipitate of 14.5g of 1-[2-(3-tert-butyl-1,2,3,4-tetrahydrocarbazole-9-yl) ethyl]pyrrolidine-N-oxide quarter-hydrate, m.p. 163–5°C.

Analysis: Found: C, 76.04; H, 9.24; N, 8.49%. Calc'd for $C_{22}H_{32}N_2O.1/4H_2O$: C, 76.58; H, 9.61; N, 8.12%.

By similar methods to that of Example 23, the products of Examples 2 to 22 are converted to their N-oxides.

EXAMPLE 24

Tablet formulation:

| | Mg/Tablet |
|---|---|
| 3-tert-butyl-9-(2-pyrrolidinoethyl)-1,2,3,4-tetrahydrocarbazole hydrochloride | 112.0* |
| dicalcium phosphate | 240.0 |
| corn starch | 20.0 |
| magnesium stearate | 3.2 |
| sodium lauryl sulfate | 0.4 |

*equivalent to 100 mg. of free base.

The ingredients are blended and compressed, broken into granules and re-compressed into finished tablets containing the requisite amount of 3-tert-butyl-9-(2-pyrrolidinoethyl)-1,2,3,4-tetrahydrocarbazole hydrochloride.

EXAMPLE 25

Capsule formulation:

| | Mg/Capsule |
|---|---|
| 3-tert-butyl-9-(2-pyrrolidinoethyl)-1,2,3,4-tetrahydrocarbazole hydrochloride | 112.0* |
| corn starch | 254.0 |
| microcrystalline cellulose | 254.0 |
| magnesium stearate | 10.8 |
| sodium lauryl sulfate | 1.2 |
| | 682.0 |

*equivalent to 100 mg. of free base.

The ingredients are blended and filled into hard gelatin capsules of suitable size to contain the requisite amount of 3-tert-butyl-9-(2-pyrrolidinoethyl)-1,2,3,4-tetrahydrocarbazole hydrochloride.

What is claimed is:

1. A compound of the formula:

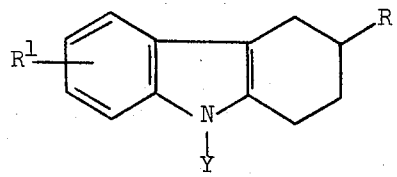

or an N-oxide or a pharmaceutically-acceptable acid addition salt thereof wherein R is alkyl of from 3 to 5 carbon atoms, R¹ is hydrogen, halogen, lower alkyl, lower alkoxy or hydroxy; and Y is aminoalkyl of the formula —Alk—NR²R³ in which R² and R³ taken separately are each lower alkyl and R² and R³ taken together with the nitrogen atom to which they are attached form a pyrrolidino, piperidino, perhydroazepino, morpholino, thiomorpholino or 1,1-dioxoperhydro-1,4-thiazino group and 'Alk' is a divalent alkyl group containing from 2 to 4 carbon atoms; or Y is an amino-cyclic group of the formula —C$_n$H$_{2n}$—C$\bigcirc$Z, in which n is 0 to 3 and Z is a divalent group which completes a pyrrolidine, piperidine or perhydroazepine ring, the nitrogen atom in said ring being separated from the nitrogen atom to which the aminocyclic group is attached by a chain of from 2 to 4 carbon atoms.

2. A compound as claimed in claim 1, in which R is a branched chain alkyl group containing a quaternary carbon atom.

3. A compound as claimed in claim 2, in which R is a tertiary butyl group.

4. A compound as claimed in claim 1, in which R¹ is hydrogen or halogen.

5. A compound as claimed in claim 1, in which Y is an aminoalkyl group —Alk—NR²R³ in which 'Alk' is ethylene or trimethylene.

6. A compound as claimed in claim 5, in which —NR²R³ is a dimethylamino, diethylamino, pyrrolidino, piperidino, perhydroazepino or morpholino group.

7. 3-Tertiary-butyl-9-(2-pyrrolidino-ethyl)-1,2,3,4-tetrahydrocarbazole, or an N-oxide or a pharmaceutically-acceptable acid addition salt thereof.

* * * * *

UNITED STATES PATENT AND TRADEMARK OFFICE
CERTIFICATE OF CORRECTION

PATENT NO. : 3,931,222
DATED : January 6, 1976
INVENTOR(S) : Peter E. Cross et al It is certified that error appears in the above–identified patent and that said Letters Patent are hereby corrected as shown below:

In the title please change "DERIVATES" to --DERIVATIVES--.

Signed and Sealed this

Twenty-first Day of December 1976

[SEAL]

Attest:

RUTH C. MASON
*Attesting Officer*

C. MARSHALL DANN
*Commissioner of Patents and Trademarks*